United States Patent [19]
Young et al.

[11] 4,150,968
[45] Apr. 24, 1979

[54] EMULSIFIABLE LIQUID CONCENTRATES CONTAINING 4-AMINO-6-T-BUTYL-3-(METHYLTHIO)-1,2,4-TRIAZIN-5-ONE AND 2-CHLORO-N-(2,6-DIETHYLPHENYL)-N-METHOXYMETHYLACETAMIDE

[75] Inventors: James W. Young, Kansas City, Mo.; Joseph Synek, Overland Park, Kans.

[73] Assignee: Mobay Chemical Corporation, Pittsburgh, Pa.

[21] Appl. No.: 874,302

[22] Filed: Feb. 1, 1978

[51] Int. Cl.² ............................................. A01N 17/08
[52] U.S. Cl. ........................................ 71/93; 71/118; 71/DIG. 1
[58] Field of Search ...................... 71/93, DIG. 1, 118

[56] References Cited

U.S. PATENT DOCUMENTS

| 3,442,945 | 5/1969 | Olin ................................... 71/93 X |
| 3,986,862 | 10/1976 | Armstrong ............................... 71/93 |

Primary Examiner—Catherine L. Mills
Attorney, Agent, or Firm—Sprung, Felfe, Horn, Lynch & Kramer

[57] ABSTRACT

Chemically and physically stable herbicidal, water-emulsifiable, liquid concentrates containing 4-amino-6-t-butyl-3-(methylthio)-1,2,4-triazin-5-one (metribuzin) and 2-chloro-N-(2,6-diethylphenyl)-N-methoxymethylacetamide (alachlor) are dissolved with an appropriate emulsifying agent in alkylbenzenes, especially xylene. The presence of the amide ingredient in about 3 to 5 times the weight of the triazinone ingredient permits the triazinone ingredient to be dissolved to the extent of as much as 12% by weight in xylene compared with only 4% in the absence of the amide.

8 Claims, No Drawings

EMULSIFIABLE LIQUID CONCENTRATES CONTAINING 4-AMINO-6-T-BUTYL-3-(METHYLTHIO)-1,2,4-TRIAZIN-5-ONE AND 2-CHLORO-N-(2,6-DIETHYLPHENYL)-N-METHOXYMETHYLACETAMIDE

FIELD OF THE INVENTION

The present invention is concerned with herbicidal compositions which are cold-stable solutions above 0° C.

BACKGROUND OF THE INVENTION

In order to make use of biologically active compounds it is often desirable to formulate them with inert carriers, for instance, organic solvents. The solubility of the active compound in its carrier determines the strength of the formulation. This formulation, whether a true solution or a dispersion, should be stable under normal conditions of shipping and storage and preferably should remain liquid at temperatures down to about 0° C.

It may also be advantageous to include more than one biologically active compound in a given formulation. The combination allows the realization of the beneficial effect of the components from a single application.

A particularly attractive herbicide for the control of weeds in connection with crops is 3-methyl-thio-4-amino-6-tert. butyl-1,2,4-triazin-5-one of the formula

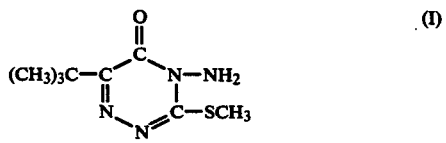

and commonly known as metribuzin. The preparation of the compound of formula I as well as herbicidal compositions containing this compound as an active ingredient are described in U.S. Pat. No. 3,961,936 Unfortunately, this compound has a high melting point (about 120° C.) and limited solubility in common organic solvents such as alkyl benzenes.

U.S. Pat. No. 3,986,862 suggests that metribuzin be combined with 2-chloro-N-(2,6-diethyl-phenyl)-N-methoxymethylacetamide of the formula

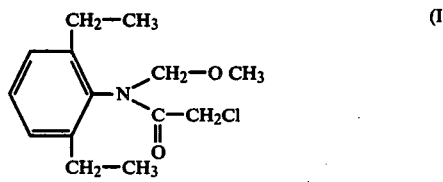

and commonly known as alachlor. The combination is reported to interact synergistically with chlorobenzene to allow higher concentrations of the active ingredients in stable solutions.

It is an object of the present invention to render metribuzin more amenable to formulation with inexpensive nonhalogenated diluents and inert carriers. It is also an object to combine metribuzin with another herbicidally active compound. Finally, it is an object of this invention to enhance the solubility of metribuzin in alkyl benzenes.

Surprisingly, it has been found that these objects may be achieved by combining metribuzin with alachlor in the presence of alkyl benzenes.

DETAILED DESCRIPTION OF THE INVENTION

When the metribuzin and alachlor are mixed at various ratios, there is little difference in the resultant final melt point of (solidification temperature) the mixtures. There is a slight depression of the melt points relative to either of the pure materials as evidenced by the following table.

| Metribuzin Tech. | Alachlor Tech. 90.2% | Melt Point of Mixture (Solidification Temp.) |
|---|---|---|
| 5% | 95% | ca. 35° C. |
| 10% | 90% | ca. 33° C. |
| 15% | 85% | ca. 31° C. |
| 20% | 80% | ca. 29° C. |
| 80% | 20% | ca. 87° C. |

Surprisingly it was found that weight ratios of metribuzin to alachlor from about 1:3 to 1:5 increase the solubility of metribuzin in alkyl benzene over that of metribuzin alone. The preferred ratio of about 1:4 gives a threefold increase in the solubility of metribuzin in alkyl benzene alone. The metribuzin-alachlor mixtures are surprisingly soluble in alkyl benzene, with about 12% by weight of metribuzin in solution at 0° C. as compared to 4% if metribuzin is dissolved alone. In addition, the alkyl benzene allows the incorporation of surfactants as well as co-solvents and couplers in a formulation without resulting in a solidification of the composition at 32° F. or above. The use of co-solvents such as glycols, glycol ethers, alcohols, ketones, etc., used in small quantities of not more than about 10% by weight may be incorporated into the formula without affecting the solubility of metribuzin in alkyl benzene. Preferred co-solvents are lower alkylene glycols and polyglycols, phenol and lower alkanol ethers thereof, water-soluble alkanols, ketones, and the like.

The selection of an alkyl benzene will depend upon availability and cost and all of the following are suitable: ortho, meta, or para-xylene and mixtures thereof; isopropyl benzene; n-propylbenzene, 1-methyl-3-ethylbenzene; 1-methyl-4-ethylbenzene; 1-methyl-2-ethylbenzene; 1,3,5-triethylbenzene, 1,2,4-triethylbenzene, alkylated heavy aromatic naphthas, and proprietary mixtures of lower alkyl benzenes such as are sold under the names Tenneco 500, Tenneco 500-100, Espesol 5, Espesol 1, Apco 100, and the like.

The selection of a suitable surfactant or mixture of surfactants to serve as emulsifying agent can be made readily by one skilled in the art in accordance with known principles as set forth in *Emulsions, Theory and Practice* by Paul Becher, 2nd Edition, Reinhold Publishing Corporation, New York, the disclosure of which is incorporated herein by reference. Suitable surfactants can also be selected from those listed in *Detergents and Emulsifiers*, published by McCutcheon's Division, Allured Publishing Corporation, New Jersey, 1972 Annual, which is also incorporated herein by reference.

The typical emulsifiers are nonionic and anionic surfactants with a hydrophilic/lipophilic balance (HLB) suitable to emulsify the concentrates of this invention in water.

Particular surfactants or emulsifiers which may be utilized include the following: ATLOX 3403F or ATLOX 3409 which are general purpose formulated nonionic and anionic emulsifiers available from ICI, United States; and GAFAC RE 610, anionic complex organic (aromatic) phosphate ester in free acid form, which is available from GAF Corporation.

The amount of emulsifer which will be utilized may vary between about 0.5 to 20% by weight, preferably about 2 to 5% by weight.

The final composition to be applied to the field can be fully compounded in advance, i.e. a "formulated" product which need only be diluted with water prior to use. Alternatively, each of the active ingredients may be separately formulated and both formulations mixed with each other and with diluent water in a tank just prior to use, i.e. "tank mixes" of the components.

To show that there were no differences between a formulated product and a tank mix, biological performance data were collected. The formulated product contained 1 lb. of metribuzin and 4 lbs. of alachlor per gallon of alkyl benzene containing surface active agents. This was compared to a tank mix from metribuzin 50% Wettable Powder and Alachlor 4 Emulsifiable. Equal total amounts of active ingredients were applied before emergence of soybeans and tomatoes and compared for phytotoxicity and on a half dozen weed species for efficacy (weed control).

The performance data were obtained 14 days after treatment by visual observations. Ratings were based on a 0–10 scale where 0 was no effect and 10 was complete plant kill. Ratings of 3 or less were obtained on soybean and tomato and were indicative of acceptable phytotoxicity; ratings of 8 or greater were obtained on weed species and were indicative of acceptable weed control. Data obtained are averages of 3 identical tests.

In general, there were only slight differences in overall weed control and phytotoxicity resulting from comparable treatments of the metribuzin/alachlor formulation and tank mix, i.e. 10% or less, indicating nearly equal activity and nearly equal phytotoxic responses.

Preparations of suitable compositions in accordance with the present invention are shown in the following examples:

EXAMPLE 1

117 Grams of technical metribuzin were mixed with 450 grams of technical alachlor, 250 grams of xylene and 50 grams of Atlox 3403 (Polyoxyethylene ether polyoxyethylene glyceride alkyl aryl sulfonate blend). The solution was heated until all materials were liquefied and then allowed to cool to room temperature.

EXAMPLE 2

Another mixture was made using 117 grams of metribuzin technical, 450 grams of alachlor technical, 206 grams xylene, 50 grams of ethylene glycol monomethyl ether and 50 grams of Atlox 3403 emulsifier. The solubility of metribuzin in xylene is raised by 300%.

It will be appreciated that the instant specification and examples are set forth by way of illustration and not limitation, and that various modifications and changes may be made without departing from the spirit and scope of the present invention.

What is claimed is:

1. A water-dispersible liquid herbicidal composition consisting essentially of
   (A) 4-amino-6-tert. butyl-3-methyl-thio-1,2,4-triazin-5-one,
   (B) about 3 to 5 times as much 2-chloro-N-(2,6-dimethylphenyl)-N-methoxymethyl-acetamide as (A),
   (C) a lower alkyl benzene, solvent and
   (D) a surfactant.

2. A composition according to claim 1, containing more than about 4% of (A) by weight.

3. A composition according to claim 1, wherein the weight ratio of (A) to (B) is about 1:4.

4. A composition according to claim 1, wherein the lower alkyl benzene is xylene.

5. A composition according to claim 1, wherein the surface active agent is a non ionic-anionic blended surface active agent.

6. A composition according to claim 5, wherein the lower alkyl benzene is xylene.

7. A composition according to claim 6, containing more than about 4% of (A) by weight.

8. A method of improving the solubility of 4-amino-6-tert.butyl-3-methyl-thio-1,2,4-triazin-5-one in a lower akyl benzene comprising also including in said lower alkyl benzene about 3 to 5 times as much 2-chloro-N-(2,6-diethylphenyl)-N-methoxymethylacetamide as 4-amino-6-tert. butyl-3-methyl-thio-1,2,4-triazin-5-one.

* * * * *

UNITED STATES PATENT AND TRADEMARK OFFICE
CERTIFICATE OF CORRECTION

PATENT NO. : 4,150,968
DATED : April 24, 1979
INVENTOR(S) : James W. Young et al It is certified that error appears in the above-identified patent and that said Letters Patent are hereby corrected as shown below:

Column 1, line 42 after "936" insert --.--.

Column 4, claim 1, lines 5-6 "dimethylpentyl" should be --diethylpentyl--.

Signed and Sealed this

Twenty-ninth Day of January 1980

[SEAL]

Attest:

SIDNEY A. DIAMOND

Attesting Officer     Commissioner of Patents and Trademarks